United States Patent [19]

Siepser

[11] Patent Number: 5,203,865
[45] Date of Patent: Apr. 20, 1993

[54] SURGICAL KNIVES FOR USE IN OPHTHALMIC SURGERY

[76] Inventor: Steven B. Siepser, 866 Downington Pike, West Chester, Pa. 19380

[21] Appl. No.: 572,173

[22] Filed: Aug. 23, 1990

[51] Int. Cl.$^5$ ............................................. A61B 17/32
[52] U.S. Cl. .................................. 606/166; 606/167; 30/162
[58] Field of Search ............... 606/166, 167, 170, 172; 30/162

[56] References Cited

U.S. PATENT DOCUMENTS

| | | | |
|---|---|---|---|
| 2,710,448 | 6/1955 | Andrews | 30/162 |
| 3,256,874 | 6/1966 | Marco | 606/170 |
| 3,945,117 | 3/1976 | Beaver | 606/172 |
| 3,967,377 | 7/1976 | Wells | 606/170 |
| 4,324,044 | 4/1982 | Shahinian, Jr. | 606/172 |
| 4,688,570 | 8/1987 | Kramer et al. | 606/172 |

FOREIGN PATENT DOCUMENTS

| | | | |
|---|---|---|---|
| 0448013 | 10/1974 | U.S.S.R. | 606/166 |
| 1533669 | 12/1989 | U.S.S.R. | 606/166 |

OTHER PUBLICATIONS

American V. Mueller (Cataloge), pp. 3 and 9, 1980.

*Primary Examiner*—C. Fred Rosenbaum
*Assistant Examiner*—William Lewis
*Attorney, Agent, or Firm*—Woodcock Washburn Kurtz Mackiewicz & Norris

[57] ABSTRACT

Surgical blades for use in ophthalmic surgery are shown to include a first shaft, a second shaft, connected to the first shaft at a predetermined angle and a tip, connected to the distal end of said second shaft. The tip associated with the micro-paufique blade has a tapered surface extending inwardly forming a continuous cutting edge which includes a front portion and first and second side portions. Rotation and transverse movement of the first shaft in relation to a scleral incision results in a subsurface scleral pocket. In a preferred embodiment the micro-paufique tip portion is generally circular shape around its outer periphery and the tapered surface extends radially inwardly and towards the bottom surface. The tip associated with the micro-keratome blade extends a distance along a central axis and includes first and second side portions substantially symmetrical to the central axis. Each of the first and second side portions includes a cutting edge oriented at a second angle with respect to the central axis. In a preferred embodiment of the micro-keratome tip the first and second side portions include a tapered surface and a generally rounded side edge, wherein the cutting edge extends to the side edge leading end and the end of the taper extends to the side edge trailing end. The tip also can include back edges which are rounded so that if the blade is retracted from an incision along the central axis, the back edges will not modify the incision.

11 Claims, 2 Drawing Sheets

SURGICAL KNIVES FOR USE IN OPHTHALMIC SURGERY

FIELD OF THE INVENTION

The present invention relates to the field of ophthalmic surgery and more particularly to intraocular surgery and finds special importance in the treatment of lens disorders, such as cataracts, which treatment utilizes phacoemulsification and artificial lens implantation techniques.

BACKGROUND OF THE INVENTION

Vision is dependent upon the eye forming an image of an object and sending that image to the sensory centers of the brain. In this process, light reflected from an object passes through the cornea, the aqueous humor, the pupil, the lens and the vitreous humor of the eye. The reflected light is focused by the lens onto the retina, thereby stimulating the optic nerve cells. In turn, the optic nerve carries messages from the nerve cells to the visual cortex of the brain. The disc-shaped lens of the eye performs the same function as the lens of a camera.

The lens, as well as other internal parts of the eye, is subject to damage by physical or other external trauma, whether accidental or otherwise, and also by the formation of cataracts. Damage to the lens can affect its accuracy in focusing light on the retina. Damage to other internal parts of the eye can also effect the ability of the eye to accurately convert light into messages for transmission to the brain.

The formation of cataracts are a common disorder of the eye, and are one of the leading causes of blindness in the United States. A cataract is a physical change in the lens characterized by a transformation of the normally transparent lens to a cloudy or opaque state. As a consequence, adequate light cannot reach the retina, and vision becomes increasingly blurred. There are several basic types of cataracts, including congenital cataracts, cataracts caused by accidental injury, cataracts caused by disease such as diabetes or glaucoma, and so-called senile cataracts which commonly appear in persons over about 65 or 70 years of age.

Lens deficiencies, such as cataracts, and other internal eye problems are generally treated by surgical procedures in which an opening is made into the eye through which other surgical procedures such as removal of the damaged lens or other repair procedures can be carried out. A number of surgical procedures to create an opening for removing a damaged lens and replacing it with an artificial lens are known. The most frequently employed and favorably regarded methodology is the extracapsular technique wherein a transverse incision is made in the limbus zone directly through the cornea into the anterior chamber. One of the major advantages of this technique is that a small incision of only about 3 mm is required to remove the natural lens from the eye and insert an artificial lens. There are, however, a number of significant disadvantages associated with the use of this type of procedure.

Specifically, transverse incisions typically require the use of a number of sutures, which can result in additional discomfort and irritation during the healing process as well as induced astigmatism. It has been discovered that the size of the incision as well as suture tension will effect the severity of any resulting astigmatism. Moreover, a significant amount of undesirable drag on the incision edges during instrument insertion has been evident.

Consequently, a need exists for a surgical procedure to create an opening in the eye utilizing a minimum length incision together with a minimum number of sutures. Such a procedure has been developed and is particularly described in my copending application identified as Attorney Document No. SIEP-1 filed concurrently herewith and incorporated herein by reference. That procedure generally involves making a radial incision into the sclera, which incision is of a depth less than the scleral thickness, the creation of a subsurface scleral pocket both laterally and inferiorly to the radial incision and the making of a transverse incision in the subsurface pocket through the cornea and into the anterior chamber. Unfortunately, currently existing surgical knives and blades are unsuitable and/or inefficient for performing this surgical procedure. Consequently, a need exists for surgical blades which are capable of creating such an opening.

SUMMARY OF THE INVENTION

The advantages of the invention are achieved in surgical blades for use in ophthalmic surgery are shown to include a first shaft, a second shaft, connected to the first shaft at a predetermined angle and a tip, connected to the distal end of said second shaft. The tip associated with the micro-paufique blade has a tapered surface extending inwardly forming a continuous cutting edge which includes a front portion and first and second side portions. Rotation and transverse movement of the first shaft in relation to a scleral incision results in a subsurface scleral pocket. In a preferred embodiment the micro-paufique tip portion is generally circular shaped around its outer periphery and the tapered surface extends radially inwardly and towards the bottom surface. The tip associated with the micro-keratome blade extends a distance along a central axis and includes first and second side portions substantially symmetrical to the central axis. Each of the first and second side portions includes a cutting edge oriented at a second angle with respect to the central axis. In a preferred embodiment of the micro-keratome tip the first and second side portions include a tapered surface and a generally rounded side edge, wherein the cutting edge extends to the side edge leading end and the end of the taper extends to the side edge trailing end. The tip also can include back edges which are rounded so that if the blade is retracted from an incision along the central axis, the back edges will not modify the incision.

The advantages of the invention are also achieved in a guarded sclerostomy surgical knife which includes a handle having a surface formed at one end and a blade, attached to the handle and positioned to extend a distance outwardly from the surface formed at the end of the handle. The distance which the blade extends is less than the thickness of the sclera so that when the knife is moved across the eye and the blade is pressed against the sclera the handle surface comes in contact with the sclera and an incision results, wherein the incision has a depth less than the sclera thickness so that penetration into the anterior chamber does not occur.

The advantages of the invention can also be achieved in a kit having component parts adapted to be used together in ophthalmic surgery to produce a sutureless opening through the sclera and into the posterior chamber. The kit is shown to include a micro-paufique blade which includes a first shaft, a second shaft, connected to the first shaft at a predetermined angle and extending a distance and a first tip, connected to the distal end of the second shaft, whereby rotation and transverse movement of the first shaft in relation to a partial incision in the sclera results in a subsurface scleral pocket, and a micro-keratome blade which includes a third shaft, a fourth shaft, connected to the third shaft at a predetermined first angle and extending a distance and a second tip, connected to the distal end of the fourth shaft and extending a distance along a central axis. The micro-keratome blade is adapted for insertion in the scleral pocket formed by the micro-paufique blade and for making a second partial incision along a line transverse to the first partial incision through the sclera and into the posterior chamber.

The kit can also include a guarded sclerostomy knife for forming a partial scleral incision having a depth less than the sclera thickness so that penetration into the anterior chamber does not occur, which partial incision can be used in relation to the micro-sclerotome blade for forming the scleral pocket.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which.

DETAILED DESCRIPTION OF THE EMBODIMENTS

Figure 1:
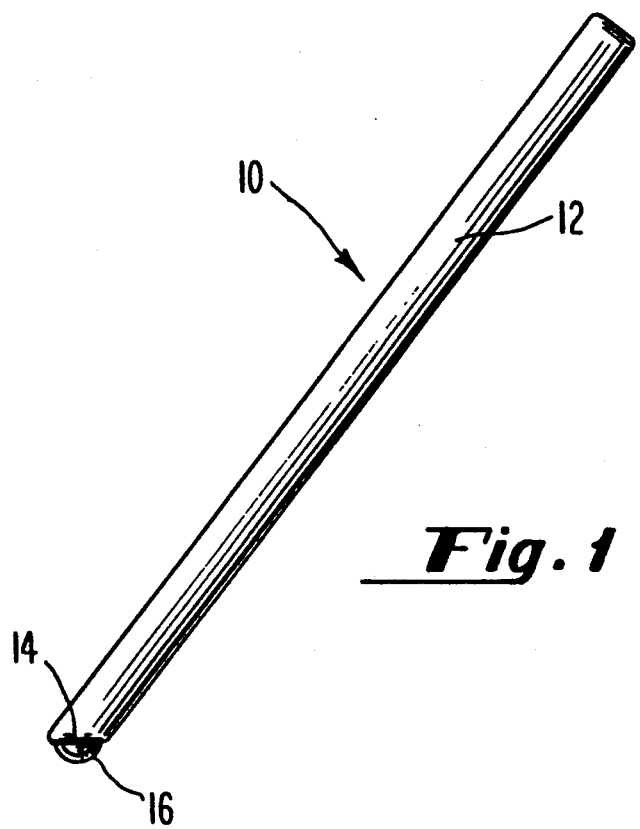
FIG. 1 is a side view of a guarded sclerotomy knife constructed in accordance with the present invention.
Figure 2:
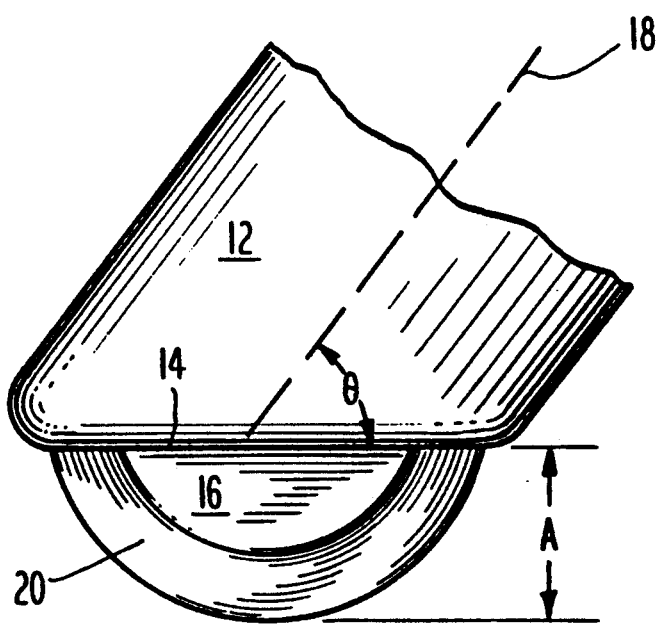
FIG. 2 is an enlarged view of the blade portion of the knife depicted in FIG. 1.

A surgical knife for use in ophthalmic surgery is shown in FIG. 1 and generally designated 10. Knife 10 is seen to include a handle 12 having a surface 14 formed at one end. A blade 16 is attached to handle 12 by any suitable means and extends a distance outwardly from surface 14. FIG. 2 is an enlarged view and more clearly shows the relationship of surface 14 and blade 16.

As shown in FIG. 2, blade 16 extends a distance "A" from surface 14, which distance is less than the thickness of the sclera of the eye. When knife 12 is moved across the eye and blade 16 is pressed against the sclera, a partial incision will result. As knife 10 is pressed against the sclera, blade 16 will penetrate until surface 14 contacts the sclera outer surface. As knife 10 is moved across the sclera and incision of uniform depth is assured so long as surface 14 is kept in contact with the outer surface of the sclera. Such an incision has a depth less than the scleral thickness such that penetration into the anterior or posterior chambers does not occur.

As shown in FIG. 2, handle 12 defines a central axis 18. Surface 14, which is substantially planar, is formed at an angle to axis 18. In the preferred embodiment, angle is the range from about 30° to about 60°. It will also be appreciated from FIG. 2, that blade 16 comprises a tip 20, which tip is arcuate shaped. In the preferred embodiment, distance "A", i.e. the distance blade 16 extends from surface 14 is approximately 3 mm.

Although distance "A" can be any distance less than the scleral thickness, it is preferred that distance "A" be approximately equal on half scleral thickness.

Figure 3:
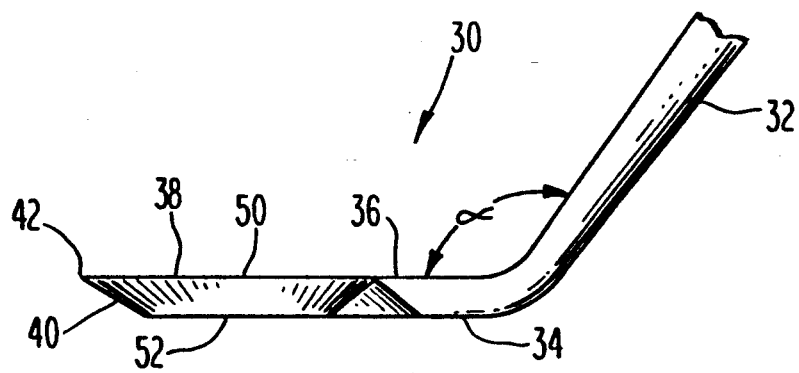
FIG. 3 is a side view of a sclerotome blade constructed in accordance with the present invention.
Figure 4:
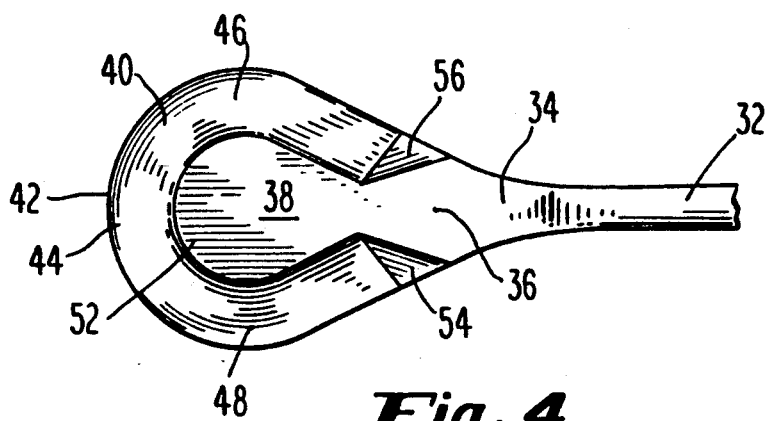
FIG. 4 is a top view of the blade depicted in FIG. 3.

Referring now to FIGS. 3 and 4, a surgical blade for use in ophthalmic surgery is shown and generally designated 30. Blade 30 is shown to include a first shaft 32 and a second shaft 34. Shaft 34 is connected to shaft 32 at a predetermined angle $\alpha$. The preferred embodiment, $\alpha$ is in the range from about 30° to about 60°. Shaft 34 extends a distance from shaft 32 forming a distal end 36. A tip 38 is connected to the distal end 36 of shaft 34.

Tip 38 is shown to have a tapered surface 40 extending inwardly and forming a continuous cutting edge 42 on tip 38. Cutting edge 42 is shown to include a front portion 44 formed at the distal end of tip 38 and two side portions 46 and 48. It is noted that if an incision is made utilizing knife 10, shown in FIGS. 2 and 3, and further if blade 30 is placed within that incision, rotation and transverse movement of shaft 32 will result in the formation of a subsurface scleral pocket. Utilization blade 30, a pocket can be simply formed on either side of the incision without modifying the incision in any way. Shaft 34 facilitates the formation of such pocket in that it permits tip 38 to have a significantly reduced size. In other words, shaft 34 facilitates the movement of tip 38 within the sclera without a need for modification of the original incision.

As particularly shown in FIG. 4, the cutting edge associated with front portion 44 and side portions 46 and 48 is arc shaped and preferably form a generally circular shape along with outer periphery of tip 38. A tapered surface 40 extends radially inwardly from such generally circular outer periphery. As shown in FIG. 3, tip 38 includes top surface 50 and bottom surface 52. Tapered surface 40 extends from cutting edge 42 towards bottom surface 52. As shown in FIG. 4, tip 38 further includes beveled portions 54 and 56 formed at the connection of tip 38 and shaft 34. It will also be appreciated from FIG. 4, that shaft 34 extends outwardly so that its sides are substantially continuous with cutting edge 42. The sides of shaft 34 are rounded. By rounding the sides of shaft 34, it is assured that cutting will only occur in relation to cutting edge 42.

In the preferred embodiment, shaft 34 is approximately 3 mm. long from the point of connection to shaft 32 to distal end 36. It is also preferred that the distance between the cutting edge on side portion 46 to the cutting edge formed on side portion 48, i.e. the diameter of the generally circular tip, be approximately 2 mm. It is still further preferred that the end of shaft 32 be approximately 0.3 mm. wide at the point of connection to shaft 34.

Figure 5:
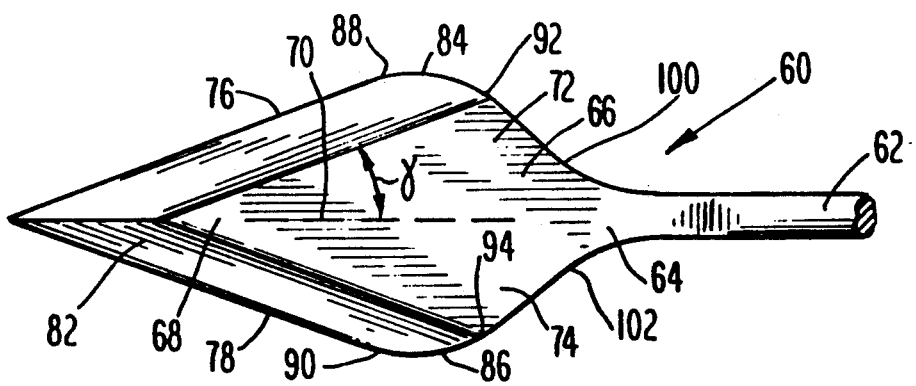
FIG. 5 is a top view of a micro-keratome blade constructed in accordance with the present invention.
Figure 6:
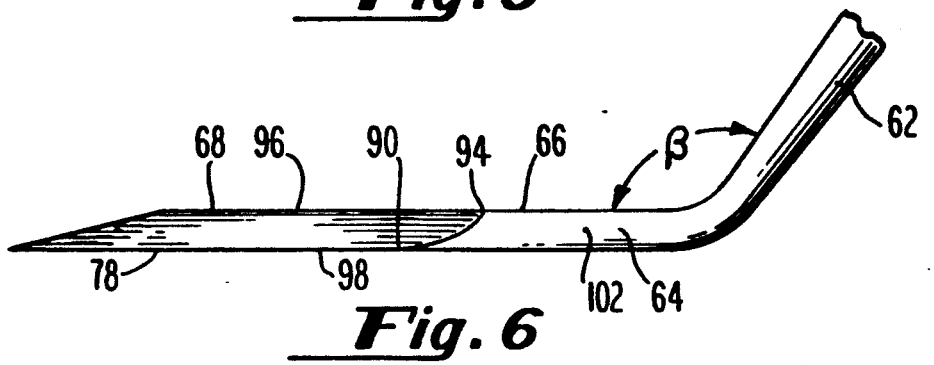
FIG. 6 is a side view of the blade depicted in FIG. 5.

Referring now FIGS. 5 and 6, a surgical blade for use in ophthalmic surgery is depicted and generally designated 60. Blade 60 is shown to include shaft 62 which is connected to shaft 64. Shaft 64 extends the distance from first shaft 62 thereby forming a distal end 66. A tip 68 is connected to distal end 66 of shaft 64. Tip 68 is shown to extend along a central axis 70.

Tip 68 is also shown in FIG. 5 as including side portions 72 and 74 which are substantially symmetrical about central axis 70. Each of side portions 72 and 74 are shown to include a cutting edge 76 and 78, which cutting edges are oriented at an angle with respect to central axis 70. Side portions 72 and 74 are also shown to include a tapered surface 80 and 82, respectively, which tapered surfaces extend away from cutting edges 76 and 78. Side portions 72 and 74 are further shown to include side edges 84 and 86, which side edges are generally rounded.

As will be appreciated by referring to both FIGS. 5 and 6, cutting edges 76 and 78 extend to the leading ends 88 and 90, respectively. It will also be seen that that portion of the tapered surfaces which is farthest from cutting edges 76 and 78 extends to the trailing ends 92 and 94 of side edges 84 and 86, respectively.

As will be appreciated from FIG. 6, tip 68 includes top surface 96 and bottom surface 98, wherein tapered surfaces 76 and 78 extend towards bottom surface 98. In other words, cutting edges 76 and 78 are formed on bottom surface 98. It will also be appreciated from FIGS. 5 and 6, that side portions 72 and 74 include back edges 100 and 102, which back edges are rounded such that if blade 60 is retracted from an incision along a path parallel to central axis 70, back edges 100 and 102 will not modify the incision, i.e. enlarge the incision or cause superficial cuts.

As shown in FIG. 6, shaft 64 and 62 are attached such that an angle β exists therebetween. It is preferred that β lie in the range from about 30° to about 60°. It is further preferred that the length of shaft 64 be approximately 3 mm. It is also preferred that the distance from side edge 84 to side edge 86 be approximately equal to 2 mm. It is still further preferred that shaft 62 be approximately 0.3 mm. wide at the point of connection to shaft 64.

It is also within the scope of the present invention to provide an intraocular surgical kit having component parts adapted to be used together in ophthalmic surgery to produce a sutureless opening in an eye for performing surgery therethrough. Such a kit would include in combination, micro-paufique blade 30 and micro-keratome blade 60. The micro-paufique blade is utilized in that rotation and transverse movement of shaft 32 in relation to a partial incision on the eye will result in a subsurface pocket. Micro-keratome blade 60 is adapted for insertion in the subsurface pocket formed by micro-paufique blade 30. Upon insertion in the subsurface pocket, micro-keratome blade 60 is operative for making a second partial incision along a line generally transverse to the first partial incision and into the eye. It will be appreciated from the above, that if the micro-keratome blade is removed along a line parallel to the incision, modifiction of the incision, i.e. superficial cuts, should not occur.

In a preferred embodiment the ophthalmic surgery kit further includes a guarded sclerostomy knife 10 for forming a partial incision. As described above, such partial incision has a depth which is less than the scleral thickness such that penetration into the anterior chamber of the eye does not occur. Such partial incision is utilized in relation to micro-paufique blade 30 for the formation of the described subsurface pockets. Utilization of the described kit will result in an opening in the eye which after removal of surgical instruments results in an incision not requiring sutures to prevent the egress of aqueour humor.

While the invention has been described and illustrated with reference to specific embodiments, those skilled in the art will recognize that modification and variations may be made without departing from the principles of the invention as described herein above and set forth in the following claims.

What is claimed is:

1. A surgical blade for use in ophthalmic surgery, comprising:

a first shaft;
   a second shaft, connected to the first shaft at a predetermined first angle and extending a distance from said first shaft thereby forming a distal end; and
   a tip, connected to the distal end of said second shaft, and extending a distance along a central axis, said tip comprising first and second side portions substantially symmetrical about said central axis, each of said first and second side portions comprises a cutting edge oriented at a second angle with respect to said central axis, a tapered surface extending away from said cutting edge and a side edge which is generally rounded wherein said cutting edge extends to the leading end of said side edge and wherein that portion of the taper farthest from said cutting edge extends to the trailing end of said side edge.

2. The blade of claim 1, wherein said tip comprises top and bottom surfaces and wherein said leading edge is formed on said bottom surface and said tapered surface further extends towards said bottom surface.

3. The blade of claim 1, wherein said first and second side portions further comprise back edges which taper inwardly from said side edges toward said central axis and wherein the sides of said back edges are rounded so that if said blade is retracted from an incision along said central axis, said back edges will not modify the incision.

4. The blade of claim 1, wherein said first angle is in the range from about 30° to about 60°.

5. The blade of claim 1, wherein the length of said second shaft is approximately 3 mm.

6. The blade of claim 1, wherein the distance from the side edge associated with said first side portion to the side edge associated with said second side portion is approximately 2 mm.

7. The blade of claim 1 wherein said first shaft is approximately 0.3 mm wide at the point of connection to said second shaft.

8. An intraocular surgical kit having component parts adapted to be used together in ophthalmic surgery to produce a sutureless opening in an eye for performing surgery therethrough, said kit comprising in combination:

a micro-paufique blade comprising: a first shaft, a second shaft, connected to the first shaft at a predetermined angle and extending a distance from said first shaft thereby forming a distal end, and a first tip, connected to the distal end of said second shaft, whereby rotation and transverse movement of said first shaft in relation to a partial incision on said eye results in a subsurface pocket; and
   a micro-keratome blade comprising: a third shaft, a fourth shaft, connected to the third shaft at a predetermined first angle and extending a distance from said third shaft thereby forming a distal end, and a second tip, connected to the distal end of said fourth shaft and extending a distance along a central axis, said micro-keratome blade being adapted for insertion in said subsurface pocket and for making a second partial incision along a line transverse to said first partial incision into said eye.

9. The kit of claim 8, further comprising a guarded sclerostomy knife for forming a partial scleral incision having a depth less than the scleral thickness so that penetration into the anterior chamber does not occur, which partial incision can be used in relation to said micro-paufique blade for forming said subsurface pocket.

10. The kit of claim 8, wherein said micro-paufique blade further comprises a tapered surface extending inwardly forming a continuous first cutting edge on said tip, said cutting edge comprising a front portion formed at the distal end of said tip and first and second side portions formed on either side of said front portion.

11. The kit of claim 8, wherein said tip comprises third and fourth side portions substantially symmetrical about said central axis, each of said third and fourth side portions comprises a second cutting edge oriented at a third angle with respect to said central axis.

* * * * *